(12) United States Patent
Wooddell et al.

(10) Patent No.: US 8,021,875 B2
(45) Date of Patent: Sep. 20, 2011

(54) METHODS FOR EXPRESSION OF TRANSGENES

(75) Inventors: Christine I. Wooddell, Madison, WI (US); Hans Herweijer, Madison, WI (US)

(73) Assignee: Roche Madison Inc., Madison, WI (US)

( * ) Notice: Subject to any disclaimer, the term of this patent is extended or adjusted under 35 U.S.C. 154(b) by 2885 days.

(21) Appl. No.: 10/229,786

(22) Filed: Aug. 27, 2002

(65) Prior Publication Data

US 2010/0120152 A1    May 13, 2010

Related U.S. Application Data

(60) Provisional application No. 60/315,410, filed on Aug. 27, 2001.

(51) Int. Cl.
  *C12N 15/00* (2006.01)
  *C12N 15/09* (2006.01)
  *C12N 15/11* (2006.01)
  *C12N 15/14* (2006.01)
  *C12N 15/85* (2006.01)

(52) U.S. Cl. .............. 435/320.1; 435/69.1; 435/325; 435/455; 536/23.1; 536/24.1

(58) Field of Classification Search ............... None
  See application file for complete search history.

(56) References Cited

U.S. PATENT DOCUMENTS 5,503,993 A * 4/1996 Hayasuke et al. ........... 435/69.8
5,648,243 A * 7/1997 Hurwitz et al. .............. 435/69.6

FOREIGN PATENT DOCUMENTS

GB        2350362        * 11/2000

* cited by examiner

*Primary Examiner* — Maria Marvich
(74) *Attorney, Agent, or Firm* — Kirk Ekena (57) ABSTRACT

The present invention relates to compositions and methods for increasing long term expression in vitro and in vivo, comprising sequences and gene expression cassettes that increase expression of genes to which they are operably linked.

5 Claims, 5 Drawing Sheets

Expression as a Function of 5' and 3' Introns

SEQUENCE LISTING

<160> NUMBER OF SEQ ID NOS: 9

<210> SEQ ID NO 1
<211> LENGTH: 42
<212> TYPE: DNA
<213> ORGANISM: Mus musculus

<400> SEQUENCE: 1
aagacaattg ataaagctgg tttgagtttt tgtcatctgg ct                42

<210> SEQ ID NO 2
<211> LENGTH: 29
<212> TYPE: DNA
<213> ORGANISM: Mus musculus

<400> SEQUENCE: 2
aggaattcga ctgggtttga attttgccc                               29

<210> SEQ ID NO 3
<211> LENGTH: 44
<212> TYPE: DNA
<213> ORGANISM: Mus musculus

<400> SEQUENCE: 3
aggcaattga gatcttttg atggcagagt tcagtttacc gggt              44

<210> SEQ ID NO 4
<211> LENGTH: 31
<212> TYPE: DNA
<213> ORGANISM: Mus musculus

<400> SEQUENCE: 4
gagaattcca caagaagaga taaagtggag c                            31

<210> SEQ ID NO 5
<211> LENGTH: 44
<212> TYPE: DNA
<213> ORGANISM: Mus musculus

<400> SEQUENCE: 5
aggcaattga ttacattaca cattctgcaa gcatagcaca gagc              44

<210> SEQ ID NO 6
<211> LENGTH: 33
<212> TYPE: DNA
<213> ORGANISM: Mus musculus

<400> SEQUENCE: 6
aggaattcta tacccttcct acagccacat act                          33

<210> SEQ ID NO 7
<211> LENGTH: 844
<212> TYPE: DNA
<213> ORGANISM: Homo sapiens

<400> SEQUENCE: 7
taacatcaca tttaaaagca tctcaggtaa ctatattttg aattttttaa aaaagtaact      60
ataatagtta ttattaaaat agcaaagatt gaccatttcc aagagccata tagaccagca    120
ccgaccacta ttctaaacta tttatgtatg taaatattag cttttaaaat tctcaaaata    180
gttgctgagt tgggaaccac tattatttct atcgattcag cagccgtaag tctaggacag    240

-continued

```
gcttaaattg ttttcactgg tgtaaattgc agaaagatga tctaagtaat ttggcattta    300
ttttaatagg tttgaaaaac acatgccatt ttacaaataa gacttatatt tgtccttttg    360
tttttcagcc taccatgaga ataagagaaa gaaatgaag atcaaaagct tattcatctg     420
tttttctttt tcgttggtgt aaagccaaca ccctgtctaa aaacataaa tttctttaat     480
cattttgcct cttttctctg tgcttcaatt aataaaaaat ggaaagaatc taatagagtg    540
gtacagcact gttattttc aaagatgtgt tgctatcctg aaaattctgt aggttctgtg    600
gaagttccag tgttctctct tattccactt cggtagagga tttctagttt cttgtgggct    660
aattaaataa atcattaata ctcttctaag ttatggatta taaacattca aaataatatt    720
ttgacattat gataattctg aataaaagaa caaaaccat ggtataggta aggaatataa    780
aacatggctt ttaccttaga aaaacaatt ctaaaattca tatggaatca aaaagagcc     840
tgca                                                                  844
```

<210> SEQ ID NO 8
<211> LENGTH: 1273
<212> TYPE: DNA
<213> ORGANISM: Homo sapiens

<400> SEQUENCE: 8

```
taacatcaca tttaaaagca tctcaggtaa ctatattttg aatttttaa aaaagtaact      60
ataatagtta ttattaaaat agcaaagatt gaccatttcc aagagccata tagaccagca    120
ccgaccacta ttctaaacta tttatgtatg taaatattag cttttaaaat tctcaaaata    180
gttgctgagt tgggaaccac tattatttct attttgtaga tgagaaaatg aagataaaca    240
tcaaagcata gattaagtaa ttttccaaag ggtcaaaatt caaaattgaa accaaggttt    300
cagtgttgcc cattgtcctg ttctgactta tatgatgcgg tacacagagc catccaagta    360
agtgatggct cagcagtgga atactctggg aattaggctg aaccacatga aagagtgctt    420
tatagggcaa aaacagttga atatcagtga tttcacatgg ttcaacctaa tagttcaact    480
catcctttcc attggagaat atgatggatc taccttctgt gaactttata gtgaagaatc    540
tgctattaca tttccaattt gtcaacatgc tgagctttaa taggacttat cttcttatga    600
caacatttat tggtgtgtcc ccttgcctag cccaacagaa gaattcagca gccgtaagtc    660
taggacaggc ttaaattgtt ttcactggtg taaattgcag aaagatgatc taagtaattt    720
ggcatttatt ttaataggtt tgaaaaacac atgccatttt acaataaga cttatatttg     780
tccttttgtt tttcagccta ccatgagaat aagagaaaga aatgaagat caaaagctta    840
ttcatctgtt tttctttttc gttggtgtaa agccaacacc ctgtctaaaa acataaatt     900
tctttaatca ttttgcctct tttctctgtg cttcaattaa taaaaaatgg aaagaatcta    960
atagagtggt acagcactgt tattttcaa agatgtgttg ctatcctgaa aattctgtag     1020
gttctgtgga agttccagtg ttctctctta ttccacttcg gtagaggatt tctagttct     1080
tgtgggctaa ttaaataaat cattaatact cttctaagtt atggattata aacattcaaa    1140
ataattttt gacattatga taattctgaa taaaagaaca aaaaccatgg tataggtaag    1200
gaatataaaa catggctttt accttagaaa aaacaattct aaaattcata tggaatcaaa    1260
aaagagcctg cag                                                       1273
```

<210> SEQ ID NO 9
<211> LENGTH: 774
<212> TYPE: DNA
<213> ORGANISM: Homo sapiens

```
<400> SEQUENCE: 9
ctgcaggctc agaggcacac aggagtttct gggctcaccc tgcccccttc caacccctca        60
gttcccatcc tccagcagct gtttgtgtgc tgcctctgaa gtccacactg aacaaacttc       120
agcctactca tgtccctaaa atgggcaaac attgcaagca gcaaacagca aacacacagc       180
cctccctgcc tgctgacctt ggagctgggg cagaggtcag agacctctct gggcccatgc       240
cacctccaac atccactcga ccccttggaa tttcggtgga gaggagcaga ggttgtcctg       300
gcgtggttta ggtagtgtga gagggtccgg gttcaaaacc acttgctggg tggggagtcg       360
tcagtaagtg gctatgcccc gaccccgaag cctgtttccc catctgtaca atggaaatga       420
taaagacgcc catctgatag ggttttttgtg gcaaataaac atttggtttt tttgttttgt       480
tttgttttgt tttttgagat ggaggtttgc tctgtcgccc aggctggagt gcagtgacac       540
aatctcatct caccacaacc ttcccctgcc tcagcctccc aagtagctgg gattacaagc       600
atgtgccacc acacctggct aattttctat ttttagtaga cacgggtttc tccatgttgg       660
tcagcctcag cctcccaagt aactgggatt acaggcctgt gccaccacac ccggctaatt       720
ttttctattt ttgacaggga cggggtttca ccatgttggt caggctggtc taga             774
```

METHODS FOR EXPRESSION OF TRANSGENES

This application claims priority benefit of U.S. Provisional Application Ser. No. 60/315,410 filed Aug. 27, 2001.

FIELD OF THE INVENTION

The present invention relates to compositions and methods for enhancing expression of a transgene in vitro and in vivo. The compositions comprise gene expression cassettes and sequences that enhance long term expression. In preferred embodiments, 3'UTRs are disclosed that increase expression of a gene to which they are operably linked.

BACKGROUND

The development of gene transfer methods into liver is very attractive because the liver is the site of production for many secreted proteins (e.g., blood clotting factors VIII and IX) as well as the site of many inherited and acquired disorders including hemophilia, hypercholester-olemia, and hepatitis. The large size of this organ and its regenerative capabilities allow for transient damage and may be exploited to enhance gene transfer. Furthermore, the recently developed technique of intravascular delivery of naked plasmid DNA expression vectors allows high efficiency transfection of hepatocytes [Zhang et al. Hum Gene Ther. 1999 10(10):1735-1737]. Despite this great promise, the challenge is to both efficiently transfer and stably express transgenes in liver.

The injection of naked plasmid DNA (pDNA) into liver or tail vein vessels leads to high levels of foreign gene expression in rodent hepatocytes. Zhang et al. [Zhang et al. Hum Gene Ther. 1999 10(10):1735-1737] observed almost milligram quantities of foreign protein could be produced from >5% of the hepatocytes one day after injection. Such levels of gene transfer are sufficient to treat several common genetic diseases. Preliminary experiments have shown that intravascular injection in mice of an expression vector in which the human factor VIII gene is under transcriptional control of the cytomegalovirus promoter resulted in plasma levels of ~500 ng/ml after one day. This level is equivalent to 100-250% of the normal human plasma levels for this protein. For hemophilia A and B, their clinical courses are greatly influenced by the percentage of normal serum levels of factor VIII or IX: <2%, severe; 2-5%, moderate; and 5-30% mild [Kay and High K. Proc Natl Acad Sci USA. 1999 96(18):9973-9975]. A gene therapy that provides these factors continuously, even at 2-5% normal levels, would tremendously improve the patients' quality of life. Therefore, if expression levels were stable, the efficiency of the current naked DNA in vivo transfection method would be sufficient for human gene therapy of hemophilia A as well as several other genetic diseases including: hemophilia B, phenylketonuria, hypercholesterolemia, urea cycle disorders and organic acidurias. Expression of these factors would ideally be sustained for the lifetime of the patient, or at least for months or years.

Unstable expression of foreign genes in the liver has been observed using both viral and non-viral approaches [Yew et al. Mol Ther. 2001 4(1):75-82; Herweijer et al. J Gene Med. 2001 3(3):280-291]. Using a variety of techniques for delivery of DNA to a cell, foreign gene expression typically falls rapidly after 1-2 days. Promoter inactivation appears be the primary cause of this initial phase of expression loss [VandenDriessche et al. Curr Gene Ther 2001 September; 1(3): 301-315]. The use of viral promoters, such as CMV, RSV, and SV40 promoters, while resulting in higher expression levels than cellular promoters in in vitro experiments, were considerably less effective in vivo. Furthermore, despite high levels of expression in vivo soon after gene transfer, expression diminished over time due to promoter shut off. Additionally, several studies have found that in vivo expression from a variety of promoters in the liver following adenoviral delivery quickly decreased within the first few days. For adenoviral delivery, unstable expression may have been partly caused by immune effects against the vector particle or viral gene products. Immune response to foreign gene products may also be partially responsible for the decreased expression of transgenes in vivo.

To overcome the shutoff of viral promoters, much work has gone into identification of promoter and enhancer sequences that might provide long term expression. Viral promoters generally expressed at very high levels one day after injection, but expression fell precipitously after day one. Conversely, tissue specific promoters, such as the liver-specific albumin promoter, often gave the desired sustained expression, but only at expression levels below therapeutic amounts [Herweijer et al. J Gene Med. 2001 3(3):280-291]. Hybrid promoters containing both viral and mammalian sequences have also been constructed in attempts to enable stable, high expression in vivo. For example, elements of the hepatitis B virus (HBV) enhancer in conjunction with the CMV promoter resulted in more sustained expression in hepatocyte cell cultures.

In eukaryotic cells, transcription of RNA polymerase II transcribed genes starts with the assembly of a preinitiation complex on the promoter of a gene. The promoter typically consists of a TATA box, CAAT sequences, and other binding motifs, called cis regulatory elements, to which transcription factors bind. The formation of this preinitiation complex is enhanced or impeded by other factors binding to the DNA. The binding of these positive and negative transcriptional regulators to the promoter and enhancer regions of a gene influences recruitment of the RNA polymerase preinitiation complex to the gene, the probability of initiation of transcription by the bound RNA polymerase, and the efficiency of the RNA polymerase in transcribing the gene. Binding of a transcriptional activator to its cognate regulatory element can also result in chromatin structure changes thus indirectly regulating gene expression. These structural changes may then enhance the probability of binding of other transcriptional activators, as in the case of tyrosine aminotransferase. The hepatic transcription factor HNF3, which has binding sites in albumin enhancers, relieves chromatin repression and thereby activates transcription [Crowe et al. J Biol Chem. 1999 274(35):25113-25120]. This form of regulation may be especially important for gene transfer vectors which, by definition, will not be in their cognate chromosomal environment. The inclusion of Locus Control Regions (LCRs) or matrix attachment regions (MARs) in pDNA expression vectors may also enhance expression of transgenes in specific tissues.

A large number of transcription factors are involved in regulating expression of genes in vivo. For instance, the following 21 liver related regulatory elements (and their respective by length) have been recognized to date: ANF (10), ANF4 (12), AT-rich (13), C/EBP (10), connexin 32 gene B2 element (24), COUP/EAR (16), DBP (13), EP (15), HLF (10), HNF1 (14), HNF3 (9), HNF4 (12), insulin response element (13), metal response element (15), methylated DNA-binding protein site (13), peroxisome proliferator response element (13), promoter linked coupling element (12), Slp gene promoter element (8), VBP (10), xenobiotic response element (10), and Y box (12) (Transcription Element Search Software, Transfac database).

BRIEF DESCRIPTION OF FIGURES

FIG. 1. Gene expression cassettes used to evaluate effect of 3'UTRs and enhancers on transcription of transgenes. CMV is the enhancer/promoter element from cytomegalovirus. 5' intron is a chimeric intron from pCI plasmid. SV40 3'UTR is the 3'UTR polyadenylation signals from SV40 virus. AFP MERIT is the alpha-fetoprotein enhancer element from −5.0 kb. MMP is the mouse minimal promoter from −281 to +39 with a G to A point mutation at position −52. h Alb 3'UTR is the human albumin 3'UTR containing a truncation of intron 14. HCR is the hepatic locus control region. m Alb Enh is the mouse albumin enhancer region from −10,284 to −9,904 (direction of insertion is indicated). hAAT is human alpha-1 antitrypsin. MCK is muscle creatine kinase. hF8 3'UTR is the human Factor VIII 3'UTR. SEAP is secreted alkaline phosphatase. hF9 is human Factor IX. hF8 is human Factor VIII (black segments in pMIR181, pMIR239, pMIR241, pMIR242, and pMIR243 indicates presence of a truncated intron). mPAH is mouse phenylalanine hydroxylase.

FIG. 4. Enhancers increase expression from the minimal albumin promoter. C57B1/6 mice were injected with 10 μg plasmid pMIR97, pMIR134, pMIR143, pMIR148, or pMIR149. The serum was collected at indicated time points and assayed for SEAP expression. Expression is shown as ng human SEAP/ml mouse serum.

FIG. 6. Expression from a vector with the ApoE HCR is stabilized by the albumin 3'UTR. C57B1/6 mice were each injected with 10 μg plasmid pMIR97, pMIR135, or pMIR159 by high pressure tail vein injection, 5 mice per sample. The serum was collected at indicated time points and assayed for SEAP expression. Expression is shown as ng human SEAP/ml mouse serum.

SUMMARY

In a preferred embodiment, we describe a process for increasing expression of a transgene comprising: construction of a gene expression cassette wherein the transgene to be expressed is operably linked to a 3' untranslated region (UTR) and delivering the gene expression cassette to an animal cell. The 3'UTR is located 3' of the transgene coding sequence and enhances transcription and expression of the gene. The 3'UTR preferably enhances long term expression of the transgene, but short term expression may also be enhanced. A preferred 3'UTR that increases long term expression of a gene to which it is operably linked is the human albumin 3'UTR. Other 3'UTR sequences, such as those from other abundant, constitutively expressed endogenous genes, may also increase long term transcription of a gene expression cassette. The 3'UTR may be a naturally occurring sequence, a modified naturally occurring sequence, a recombinant, chimeric, or heterologous sequence, or a synthetic sequence. An example of a modified sequences is a sequence that contains an internal deletion. The internal deletion may remove transcription repressing sequences or reduce the size or length of the 3'UTR. A synthetic 3'UTR contains sequence that is not present in a naturally occurring 3'UTR.

In a preferred embodiment, we describe a process for increasing expression of a transgene comprising: construction of a gene expression cassette wherein the 3'UTR contains an intron and delivering the cassette to an animal cell. The intron may be a natural intron, a modified natural intron, a recombinant or chimeric intron, or a synthetic intron. An example of a modified intron is an intron that contains an interval deletion. The internal deletion may remove transcription repressing sequences or reduce the size or length of the intron. A synthetic intron contains sequence that is not present in a natural intron. The presence of the intron in the 3'UTR preferably enhances long term expression of the transgene in the gene expression cassette, but short term expression may also be enhanced. A preferred intron is intron 14 from the human albumin gene. This intron may have an internal deletion.

In a preferred embodiment, we describe a process for increasing expression of a transgene comprising: construction of a gene expression cassette wherein an intron is present near the stop codon of the gene coding sequence and delivering the cassette to an animal cell. The intron may be present within the coding sequence or in the 3'UTR. The intron may be a natural intron, a modified natural intron, a recombinant or chimeric intron, or a synthetic intron. An example of a modified intron is an intron that contains an internal deletion. The internal deletion may remove transcription repressing sequences or reduce the size or length of the intron.

In a preferred embodiment, we describe a nucleic acid sequence that enhances the long term expression of a gene when operably linked to the 3' end of the gene and the gene is delivered to a cell. The sequence comprises the albumin 3'UTR, or modifications thereof. For instance, the albumin 3'UTR may contain an internal deletion within the 3'UTR intron. Alternatively, the sequence comprises any intron located within the 3'UTR of a gene expression cassette. A preferred intron is the human albumin gene intron 14. The sequence is operably linked to a transgene and the gene expression cassette is delivered to a mammalian cell wherein expression of the transgene alters the endogenous properties of the cell. The albumin 3'UTR or the 3' intron may be used in combination with other transcription enhancing sequences selected from the group comprising: enhancers, promoters, and 5' introns (including chimeric introns).

In a preferred embodiment, it may be desirable to include, with the transcription enhancing 3'UTR, sequences downstream of the 3'UTR polyadenylation signal(s) that are not transcribed but are used for transcription termination. Such sequences may increase transcription by promoting efficient and proper termination of transcription at the end of the gene. It may also be desirable to include sequences downstream of the 3'UTR that are not transcribed but which are recognition sites for transcription activators.

The 3'UTR or 3' intron may be used to increase expression levels, increase long term expression or both of a gene expression cassette that is integrated into the genome of a cell. The 3'UTR or 3' intron may also be used to increase expression levels, increase long term expression or both of a gene expression cassette that is present on a closed circular (plasmid) DNA or on linear DNA. The 3'UTR or 3' intron may also be incorporated into viral vectors. The DNA may be delivered to a cell that is in vivo, in situ, ex vivo or in vitro.

In a preferred embodiment, we describe a gene expression cassette that enables long term expression of a transgene when delivered to a cell. The cassette comprises: an enhancer, a promoter, a 5' intron, a linker, and a 3'UTR containing an intron. The coding sequence of a desired transgene to be expressed is cloned into the linker of the expression cassette. The 3'UTR contains sequences that enhance long term expression. These sequences are selected from the group comprising: enhancer sequences, transcription activator binding sites, introns, polyadenylation signals, and transcription termination signals. A preferred 3'UTR is the albumin 3'UTR. A preferred albumin 3'UTR is the human albumin 3'UTR. The human albumin 3'UTR may be modified by deletion of a portion of intron 14 contained within the UTR. Specifically, by 185-520 of intron 14 may be removed. A preferred enhancer is the alpha-fetoprotein enhancer, the albumin enhancer, or the ApoE hepatic control region. A preferred promoter is the albumin promoter or the alpha1-antitrypsin promoter. The murine albumin minimal promoter, −281 to +39 preferably contains a GATC to AATC mutation at position −52--49 (in the HNF1 binding site). The 3'UTR may be combined with other promoter, enhancer, intron, or other transcription factor binding sequences, including tissue specific elements. The sequences may be natural or synthetic. The vector is delivered to a cell wherein the gene is expressed. A preferred cell is a liver cell. A preferred liver cell is a hepatocyte. The hepatocyte may be in vivo, ex vivo, in situ, or in vitro. Different 3'UTRs or 3' introns may best enhance transcription of transgenes in different tissues. Addition of non-GC-rich sequence to the 5 and/or 3' end to the expression cassette may improve expression of the transgene.

In a preferred embodiment, the described gene expression cassette may be used not only in non-viral expression vectors, but also in viral vectors.

In a preferred embodiment, the invention provides methods to enable long term expression of transgenes at therapeutic levels for gene therapy as well as for other research or commercial applications. Long term expression may be useful for treating genetic disorders, inducing an immune response for genetic vaccines in human and other animals, producing beneficial proteins or RNAs in animals culture cells in vitro, or for creating genetically modified animals.

Further objects, features, and advantages of the invention will be apparent from the following detailed description when taken in conjunction with the accompanying drawings.

DETAILED DESCRIPTION

The term gene generally refers to a nucleic acid sequence that comprises sequences necessary for the expression or production of a nucleic acid (e.g., RNA), polypeptide (protein) or precursor polypeptide. The polypeptide can be encoded by a full length coding sequence or by any portion of the coding sequence so long as the desired activity or functional properties (e.g., enzymatic activity, ligand binding, signal transduction) of the full-length polypeptide or fragment are retained. The term also encompasses sequences located adjacent to the coding region on both the 5' and 3' ends for a distance of about 1 kb or more on either end such that the gene corresponds to the length of the full-length mRNA. The term gene encompasses both cDNA and genom is forms of a gene. A genomic form or clone of a gene contains the coding region interrupted with non-coding sequences termed introns (also called intervening regions or intervening sequences). Introns are segments of a gene which are transcribed into RNA but are removed or "spliced out" from the primary transcript. Introns are therefore absent from messenger RNA (mRNA) transcripts. Introns may contain regulatory elements such as enhancers. The mRNA functions during translation to specify the sequence or order of amino acids in a nascent polypeptide. The term non-coding sequences also refers to other regions of a genomic form of a gene including, but not limited to, promoters, enhancers, transcription factor binding sites, polyadenylation signals, internal ribosome entry sites, silencers, insulating sequences, UTRs, LCRs, and MARs. These sequences may be present close to the coding region of the gene (within 10,000 nucleotide) or at distant sites (more than 10,000 nucleotides). These non-coding sequences influence the level or rate of transcription and translation of the gene [Xu et al. Gene. 2001 272(1-2):149-56]. Covalent modification of a gene may influence the rate of transcription (e.g., methylation of genomic DNA), the stability of mRNA (e.g., length of the 3' polyadenosine tail), rate of translation (e.g., 5' cap), nucleic acid repair, and immunogenicity. One example of covalent modification of nucleic acid involves the action of Label-IT reagents (Mirus Corporation, Madison, Wis.).

A nucleic acid can be delivered to a cell to express an exogenous nucleotide sequence, a transgene, to inhibit, eliminate, augment or alter expression of an endogenous nucleotide sequence, or to affect a specific physiological characteristic not naturally associated with the cell. Nucleic acids may contain an expression cassette coded to express a whole or partial protein, or RNA. A gene expression cassette refers to a natural or recombinantly produced nucleic acid that is capable of expressing a gene(s). A transgene is a component in a gene expression cassette. The term recombinant as used herein refers to a nucleic acid molecule that is comprised of segments of polynucleotide joined together by means of molecular biological techniques. The gene expression cassette contains the coding region of the gene of interest along with other sequences that affect expression of the gene. An expression cassette typically includes a promoter (allowing transcription initiation) and a sequence encoding one or more proteins. Optionally, the expression cassette may include, but is not limited to: enhancers, transcriptional enhancer binding sites, 5' and 3' non-coding sequences, 5' and 3' untranslated regions (UTRs), introns, splicing signals, internal ribosome entry sites (IRES), translation termination signals, polyadenylation signals, and transcription termination signals. Additionally the expression cassette may contain one or more linkers, especially between the promoter and the 3'UTR. A linker is a DNA sequence that is a recognition site for a specific restriction endonuclease and facilitates insertion of a desired coding sequence into the cassette by cloning methods standard in the art. An RNA expression cassette typically includes a translation initiation codon (allowing translation initiation), and a sequence encoding one or more proteins. Optionally, the RNA expression cassette may include, but is not limited to, translation termination signals, polyadenylation signals(s), internal ribosome entry sites (IRES), and untranslated sequences.

The nucleic acid may contain sequences that do not serve a specific function in the target cell but are used in the generation of the nucleic acid. Such sequences include, but are not limited to, sequences required for replication or selection of the nucleic acid in a host organism.

As used herein, the term gene expression refers to the process of converting genetic information encoded in a gene into RNA (e.g., mRNA, rRNA, tRNA, siRNA, or snRNA), through transcription of a deoxyribonucleic gene (e.g., via the enzymatic action of an RNA polymerase), and/or protein through translation of mRNA. Gene expression can be regulated at many stages in the process including, but not limited to, increasing transcription initiation, transcription elongation, transcription re-initiation, post-transcriptional RNA processing, transcription termination efficiency, RNA nuclear export, RNA stability, and RNA translation, and altering chromatin structure. Up-regulation or activation refers to regulation that increases the production of gene products (i.e., RNA or protein). Down-regulation or repression refers to regulations that decrease production. Molecules (e.g., transcription factors) that are involved in up-regulation or down-regulation are often called transcription enhancers or activators and transcription repressors, respectively. Nucleic acid sequences to which transcription factors, activators or repressors, bind are called binding sites or sequences or recognition sites or sequences. Gene expression may be increased by sequences whose presence results in alteration of chromatin structure.

The term nucleic acid, or polynucleotide, is a term of art that refers to a polymer containing at least two nucleotides. Natural nucleotides contain a deoxyribose (DNA) or ribose (RNA) group, a phosphate group, and a base. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups such as, but not limited to, amines, alcohols, thiols, carboxylates, and alkylhalides. The term base encompasses any of the known base analogs of DNA and RNA including, but not limited to, 4-acetylcytosine, 8-hydroxy-N6-methyladenosine, aziridinylcytosine, pseudoisocytosine, 5-carboxyhydroxylmethyl-uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, β-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. Nucleotides are the monomeric units of nucleic acid polymers and are linked together through the phosphate groups. Polynucleotides with less than 120 monomeric units are often called oligonucleotides. The term polynucleotide includes deoxyribonucleic acid (DNA) and ribonucleic acid (RNA). Natural polynucleotides have a ribose-phosphate backbone. An artificial or synthetic polynucleotide is any polynucleotide that is polymerized in vitro and contains the same or similar bases but may contain a backbone of a type other than the natural ribose-phosphate backbone. These backbones include, but are not limited to: PNAs (peptide nucleic acids), phosphorothioates, phosphorodiamidates, morpholinos, and other variants of the phosphate backbone of natural polynucleotides.

DNA may be in form of cDNA, in vitro polymerized DNA, plasmid DNA, parts of a plasmid DNA, genetic material derived from a virus, linear DNA, vectors (P1, PAC, BAC, YAC, artificial chromosomes), expression cassettes, chimeric sequences, recombinant DNA, chromosomal DNA, an oligonucleotide, anti-sense DNA, or derivatives of these groups. RNA may be in the form of oligonucleotide RNA, tRNA (transfer RNA), snRNA (small nuclear RNA), rRNA (ribosomal RNA), mRNA (messenger RNA), in vitro polymerized RNA, recombinant RNA, chimeric sequences, anti-sense RNA, siRNA (small interfering RNA), ribozymes, or derivatives of these groups. An anti-sense polynucleotide is a polynucleotide that interferes with the function of DNA and/or RNA. Interference may result in suppression of expression. The polynucleotide can also be a sequence whose presence or expression in a cell alters the expression or function of cellular genes or RNA. In addition, DNA and RNA may be single, double, triple, or quadruple stranded.

A delivered nucleic acid can stay within the cytoplasm or nucleus apart from the endogenous genetic material. Alternatively, DNA can recombine with (become a part of) the endogenous genetic material. Recombination can cause DNA to be inserted into chromosomal DNA by either homologous or non-homologous recombination.

A transfection reagent is a compound or compounds that bind(s) to or complex(es) with oligonucleotides and polynucleotides, and mediates their entry into cells. Examples of transfection reagents include, but is not limited to: cationic lipids and liposomes, polyamines, calcium phosphate precipitates, histone proteins, polyethylenimine, and polylysine complexes. It has been shown that cationic proteins like histones and protamines, or synthetic polymers like polylysine, polyarginine, polyornithine, DEAE dextran, polybrene, and polyethylenimine may be effective intracellular delivery agents, while small polycations like spermine are ineffective. Typically, the transfection reagent has a component with a net positive charge which binds to the oligonucleotide's or polynucleotide's negative charge. The transfection reagent mediates binding of oligonucleotides and polynucleotides to cells via its positive charge (that binds to the cell membrane's negative charge) or via ligands that bind to receptors in the cell. For example, cationic liposomes or polylysine complexes have net positive charges that enable them to bind to DNA or RNA. Polyethylenimine, which facilitates gene transfer without additional treatments, probably disrupts endosomal function itself.

A promoter is a nucleic acid sequence upstream of a transcribed gene that is the initial binding site for components of the RNA polymerase holoenzyme complex prior to initiation of transcription. The promoter often contains a TATA box sequence and/or an initiator sequence. The promoter typically includes many transcription factor binding sites and the position of such elements is important. Promoter elements can also be downstream of the transcription start site.

An enhancer is a DNA sequence to which transcription factors/activators bind to increase expression of a gene. The sequence may be located upstream, downstream, within an intron, in 5' or 3' untranslated regions, or within the coding sequence of a gene. The transcription activators affect recruitment of components of the RNA polymerase complex to the promoter, can affect recruitment of chromatin remodeling factors and RNA processing or export factors, or affect processivity of the RNA polymerase.

The 3'UTR is the nucleic acid sequence downstream (3') of the coding region of gene that is not translated into protein but affects expression of the gene. The 3'UTR may contain both sequences that are transcribed into RNA and sequences that are not transcribed into RNA. The 3'UTR may contain sequences that affect transcription of the gene. The 3'UTR may also contain sequences that affect stability, localization, or translation of the transcribed RNA. Components of 3'UTRs comprise: polyadenylation signals, RNA processing signals, transcription termination signals, enhancer sequences, introns and other protein binding sites.

The coding sequence of a gene is the portion of the gene that is translated into protein or polypeptide during translation of mRNA transcribed from the gene.

Polyadenylation is the addition of polyadenylic acid to the 3' end of a eukaryotic RNA after its transcription. A polyadenylation signal is a nucleic acid sequence that signals cellular machinery to add the polyadenylic acid to the RNA.

A transcription termination signal is a nucleic acid sequence that signals the halt of transcription of the DNA by the RNA polymerase and release of the newly transcribed RNA from the DNA.

Tissue specific elements are elements that predominantly function in a subset of cells in an animal, such as a tissue, but do not function equally in all cells of the animal.

Albumin Gene Family

The serum albumin gene is part of a multi-gene family that also includes alpha-fetoprotein (AFP), alpha-albumin, and the vitamin D-binding protein (also called GC) at the same gene locus [Nishio et al. J Mol Biol. 1996 259(1):113-119]. AFP is expressed in the fetus and then down-regulated shortly after birth. Serum albumin is expressed in the fetus and then continues to be expressed at very high levels throughout the life of the animal.

Albumin Gene Promoters and Enhancers

The human albumin promoter consists of 486 by upstream of the transcription start site. Two known enhancer elements are 1.7 kb and 6 kb upstream of the start site. The minimal mouse albumin promoter for tissue-specific transcription of the albumin gene is 0.3 kb and the mouse albumin enhancer is 10 kb upstream of the transcription start site [Pinkert et al. Genes Dev. 1987 1(3):268-276]. The minimal rat album in promoter requires 150 by upstream of the transcription start site. Bacterial methylation of plasmids containing the rat albumin promoter causes a severe reduction in expression. When the plasmids are grown in bacterial cells, the HNF1 transcription factor binding site in the rat albumin promoter becomes methylated in the GATC sequence. This methylation inhibits binding of the liver-specific transcription factor HNF1. A point mutation changing the G at −53 to A eliminated the GATC methylation of plasmid DNA and allowed the rat albumin promoter to function in mammalian cells [Vorachek et al. J Biol Chem 2000 275(37):29031-29041]. In our studies in mouse liver cells, the wild-type mouse albumin promoter gave low expression of two different reporter genes. A point mutation of G to A that changed the GATC in the HNF1 binding site of the mouse albumin promoter resulted in much higher basal transcription. The plasmids described in the present invention had the mouse albumin promoter with the G to A change.

AFP Enhancers

The AFP enhancers are intergenic between the 3' end of the albumin gene and the 5' end of the AFP gene. These enhancers are active with both the AFP promoter and the albumin promoter, and are proposed to serve as a locus control region [Camper and Tilghman. Genes Dev. 1989 3(4):537-546]. Three minimal AFP enhancer elements from the mouse gene were defined by Godbout et al. [Godbout et al. Mol Cell Biol. 1988 8(3):1169-1178], and are called MERI, MERII, and MERIII.

The albumin 3'UTR consists of nucleic acid sequence downstream from the albumin translation termination (stop) codon. In the present invention, the modified albumin 3'UTR sequence (SEQ ID 7) includes: 26 by of exon 14, including the translation stop codon; the first 184 by and last 151 by of intron 14 (internal 335 by deleted); and 376 by of exon 15, including 3 polyadenylation signals (polyA sites) and 97 by after the third polyA site. This 3'UTR was inserted into an expression cassette so that it was located 3' (downstream) of a reporter gene to be expressed. The albumin 3'UTR may also comprise a complete intron 14 or other internal deletions of intron 14. Additional 3' untranscribed genomic sequence may also be included. The polyA sites may be substituted for recombinant polyA sequences from other genes or with artificial polyA sites. Additional regulating sequences, including heterologous sequences, may also be added.

Long term expression means that the gene is expressed for at least 2 weeks with a less than 10 fold decrease in expression from day 1 to day 7. In contrast, expression from typical CMV promoter driven gene expression cassettes typically drops by up to 1000-fold after 7 days. For the expression cassettes containing an expression enhancing 3'UTR described herein, we have observed expression for 6 weeks and longer with less than a 10-fold drop in expression from day 1. Some of the expression cassettes have given expression for longer than 20 weeks with a less than 2-fold decrease. For expression cassettes containing similar promoters and enhancers, but without the 3'UTR, expression drops by more than 10-fold by the second week.

The cell to which the gene expression cassette is delivered can be an animal cell that is maintained in tissue culture such as cell lines that are immortalized or transformed. These include a number of cell lines that can be obtained from American Tissue Culture Collection (Bethesda) such as 3T3 (mouse fibroblast) cells, Rat1 (rat fibroblasts) cells, CV-1 (monkey kidney) cells, COS (monkey kidney) cells, 293 (human embryonic kidney) cells, HeLa (human cervical carcinoma) cells, HepG2 (human hepatocyte) cells, Sf9 (insect ovarian epithelial) cells and the like. The cell can also be a primary or secondary cell which means that the cell has been maintained in culture for a relatively short time after being obtained from an animal tissue. These include primary liver cells, primary muscle cells and the like. The cells within the tissue are separated by mincing and digestion with enzymes such as trypsin or collagenases which destroy the extracellular matrix. Tissues consist of several different cell types and purification methods such as gradient centrifugation or antibody sorting can be used to obtain purified amounts of the preferred cell type. For example, primary myoblasts are separated from contaminating fibroblasts using Percoll (Sigma) gradient centrifugation.

The terms therapeutic and therapeutic levels are defined in this application as an amount of a gene product expressed in a cell or secreted from a cell that has a reasonable expectation of beneficial result. Levels of expression of a delivered reporter gene can be measured, which correlate with a reasonable expectation of similar amounts of gene expression when delivering other transgenes. Levels of treatment considered beneficial by a person having ordinary skill in the art of gene therapy differ from disease to disease. For example, hemophilia A and B are caused by deficiencies of the X-linked clotting factors VIII and IX, respectively. Their clinical course is greatly influenced by the percentage of normal serum levels of factor VIII or IX: <2%, severe; 2-5%, moderate; and 5-30% mild. Thus, in severe patients, an increase from 1% to 2% of the normal level can be considered beneficial. Levels greater than 6% prevent spontaneous bleeds but not those secondary to surgery or injury. A person having ordinary skill in the art of gene therapy would reasonably anticipate beneficial levels of expression of a gene specific for a disease based upon sufficient levels of marker gene results. In the hemophilia example, if marker genes were expressed to yield a protein at a level comparable in volume to 2% of the normal level of factor VIII, it can be reasonably expected that the gene coding for factor VIII would also be expressed at similar levels.

There are three types of reporter (marker) gene products that are expressed from reporter genes. Since reporter genes are expressed using the same cellular machinery as endogenous genes or therapeutic transgenes, their expression is well accepted in the art as being indicative of expression that would be expected using a therapeutic transgene in a similar gene expression cassette. The reporter gene/protein systems include:

a) Intracellular gene products such as luciferase, β-galactosidase, or chloramphenicol acetyl transferase. Typically, they are enzymes whose enzymatic activity can be easily measured.
b) Intracellular gene products such as β-galactosidase or green fluorescent protein that identify cells expressing the reporter gene. On the basis of the intensity of cellular staining, these reporter gene products also yield qualitative information concerning the amount of foreign protein produced per cell.
c) Secreted gene products such as secreted alkaline phosphatase (SEAP), growth hormone, factor IX, or alpha1-antitrypsin are useful for determining the amount of a secreted protein that a gene transfer procedure can produce. The reporter gene product can be assayed in a small amount of blood.

EXAMPLES

1) Enhancers and Other Elements:
a) The murine alpha-fetoprotein (AFP) minimal enhancer from −2.5 kb, AFP MER I [Godbout et al. Mol Cell Biol. 1988 8(3):1169-1178], was generated by PCR amplification of a bacterial artificial chromosome (BAC) containing murine genomic DNA (Research Genetics BAC clone 295N4) using the primers: 5'-aagacaattgATAAAGCTG-GTTTGAGTTTTTGTCATCTGGCT-3' (SEQ ID 1) and 5'-aggaattCGACTGGGTTTGAATTTTGCCC-3' (SEQ ID 2). Mun I and EcoR I restriction sites were included for cloning purposes.
b) The murine alpha-fetoprotein (AFP) enhancer element from −5.0 kb, AFP MER II, was generated by PCR amplification of a BAC clone 295N4 containing murine genomic DNA using the primers: 5'-aggcaattgagATCTTTTTGATG-GCAGAGTTCAGTTTACCGGGT-3' (SEQ ID 3) and 5'-gagaattCCACAAGAAGAGATAAAGTGGAGC-3' (SEQ ID 4). Mun I, Bgl II, and EcoR I restrictions site were included for cloning purposes.

c) A longer murine alpha-fetoprotein (AFP) enhancer fragment that included both MER I and MER II, was generated by PCR amplification of a BAC clone 295N4 containing murine genomic DNA using the primers: 5'-aggcaat-tgagATCTTTTTGATGGCAGAGTTCAGTTTACCGGGT-3' (SEQ ID 3) and 5'-aggaattC-GACTGGGTTTGAATTTTGCCC-3' (SEQ ID 2). Mun I, Bgl II, and EcoR I restrictions site were included for cloning purposes.
d) The murine albumin enhancer (−10,284 to −9,904 bp) was generated by PCR amplification of a BAC clone 295N4 containing murine genomic DNA using the primers: 5'-ag-gcaattGATTACATTACACATTCTG-CAAGCATAGCACAGAGC-3' (SEQ ID 5) and 5'-aggaat-TCTATACCCTTTCTACAGCCACATACT-3' (SEQ ID 6). Mun I and EcoR I restriction sites were included for cloning purposes.
e) Sequence of Human Albumin Gene 3 Untranslated Region (UTR) containing a Truncation in Intron 14 (SEQ ID 7). The albumin 3'UTR construct contains 26 by of the human albumin gene exon 14 that includes the translation stop, the first 184 by and the last 151 by of intron 14 (with the internal 335 by deleted of the 770 by intron), and exon 15, which includes three polyadenylation signals and an additional 97 by after the last polyA site (376 by total exon size):

5'-TAACATCACATTTAAAAGCATCTCAGGTAACTATATTTTGAATTTTT

TAAAAAAGTAACTATAATAGTTATTATTAAAATAGCAAAGATTGACCATT

TCCAAGAGCCATATAGACCAGCACCGACCACTATTCTAAACTATTTATGT

ATGTAAATATTAGCTTTTAAAATTCTCAAAATAGTTGCTGAGTTGGGAAC

CACTATTATTTCTATCGATTCAGCAGCCGTAAGTCTAGGACAGGCTTAAA

TTGTTTTCACTGGTGTAAATTGCAGAAAGATGATCTAAGTAATTTGGCAT

TTATTTTAATAGGTTTGAAAAACACATGCCATTTTACAAATAAGACTTAT

ATTTGTCCTTTTGTTTTTCAGCCTACCATGAGAATAAGAGAAAGAAAATG

AAGATCAAAAGCTTATTCATCTGTTTTTCTTTTTCGTTGGTGTAAAGCCA

ACACCCTGTCTAAAAAACATAAATTTCTTTAATCATTTTGCCTCTTTTCT

CTGTGCTTCAATTAATAAAAAATGGAAAGAATCTAATAGAGTGGTACAGC

ACTGTTATTTTTCAAAGATGTGTTGCTATCCTGAAAATTCTGTAGGTTCT

GTGGAAGTTCCAGTGTTCTCTCTTATTCCACTTCGGTAGAGGATTTCTAG

TTTCTTGTGGGCTAATTAAATAAATCATTAATACTCTTCTAAGTTATGGA

TTATAAACATTCAAAATAATATTTTGACATTATGATAATTCTGAATAAAA

GAACAAAAACCATGGTATAGGTAAGGAATATAAAACATGGCTTTTACCTT

AGAAAAAACAATTCTAAAATTCATATGGAATCAAAAAAGAGCCTGCA-3' f) Sequence of the entire Human Albumin Gene 3' Untranslated Region (SEQ ID 8).

5'-TAACATCACATTTAAAAGCATCTCAGGTAACTATATTTTGAATTTTT

TAAAAAAGTAACTATAATAGTTATTATTAAAATAGCAAAGATTGACCATT

TCCAAGAGCCATATAGACCAGCACCGACCACTATTCTAAACTATTTATGT

ATGTAAATATTAGCTTTTAAAATTCTCAAAATAGTTGCTGAGTTGGGAAC

CACTATTATTTCTATTTTGTAGATGAGAAAATGAAGATAAACATCAAAGC

ATAGATTAAGTAATTTTCCAAAGGGTCAAAATTCAAAATTGAAACCAAGG

-continued

```
TTTCAGTGTTGCCCATTGTCCTGTTCTGACTTATATGATGCGGTACACAG

AGCCATCCAAGTAAGTGATGGCTCAGCAGTGGAATACTCTGGGAATTAGG

CTGAACCACATGAAAGAGTGCTTTATAGGGCAAAAACAGTTGAATATCAG

TGATTTCACATGGTTCAACCTAATAGTTCAACTCATCCTTTCCATTGGAG

AATATGATGGATCTACCTTCTGTGAACTTTATAGTGAAGAATCTGCTATT

ACATTTCCAATTTGTCAACATGCTGAGCTTTAATAGGACTTATCTTCTTA

TGACAACATTTATTGGTGTGTCCCCTTGCCTAGCCCAACAGAAGAATTCA

GCAGCCGTAAGTCTAGGACAGGCTTAAATTGTTTTCACTGGTGTAAATTG

CAGAAAGATGATCTAAGTAATTTGGCATTTATTTTAATAGGTTTGAAAAA

CACATGCCATTTTACAAATAAGACTTATATTTGTCCTTTTGTTTTTCAGC

CTACCATGAGAATAAGAGAAAGAAAATGAAGATCAAAAGCTTATTCATCT

GTTTTTCTTTTTCGTTGGTGTAAAGCCAACACCCTGTCTAAAAAACATAA

ATTTCTTTAATCATTTTGCCTCTTTTCTCTGTGCTTCAATTAATAAAAAA

TGGAAAGAATCTAATAGAGTGGTACAGCACTGTTATTTTTCAAAGATGTG

TTGCTATCCTGAAAATTCTGTAGGTTCTGTGGAAGTTCCAGTGTTCTCTC

TTATTCCACTTCGGTAGAGGATTTCTAGTTTCTTGTGGGCTAATTAAATA

AATCATTAATACTCTTCTAAGTTATGGATTATAAACATTCAAAATAATAT

TTTGACATTATGATAATTCTGAATAAAAGAACAAAAACCATGGTATAGGT

AAGGAATATAAAACATGGCTTTTACCTTAGAAAAAACAATTCTAAAATTC

ATATGGAATCAAAAAAGAGCCTGCAG-3'
``` g) ApoE Hepatic Control Region (HCR). The ApoE HCR was derived by PCR from human genomic DNA (SEQ ID 9):

```
5'-CTGCAGGCTCAGAGGCACACAGGAGTTTCTGGGCTCACCCTGCCCCC

TTCCAACCCCTCAGTTCCCATCCTCCAGCAGCTGTTTGTGTGCTGCCTCT

GAAGTCCACACTGAACAAACTTCAGCCTACTCATGTCCCTAAAATGGGCA

AACATTGCAAGCAGCAAACAGCAAACACACAGCCCTCCCTGCCTGCTGAC

CTTGGAGCTGGGGCAGAGGTCAGAGACCTCTCTGGGCCCATGCCACCTCC

AACATCCACTCGACCCCTTGGAATTTCGGTGGAGAGGAGCAGAGGTTGTC

CTGGCGTGGTTTAGGTAGTGTGAGAGGGTCCGGGTTCAAAACCACTTGCT

GGGTGGGGAGTCGTCAGTAAGTGGCTATGCCCCGACCCCGAAGCCTGTTT

CCCCATCTGTACAATGGAAATGATAAAGACGCCCATCTGATAGGGTTTTT

GTGGCAAATAAACATTTGGTTTTTTGTTTTGTTTTGTTTTGTTTTTTGA

GATGGAGGTTTGCTCTGTCGCCCAGGCTGGAGTGCAGTGACACAATCTCA

TCTCACCACAACCTTCCCCTGCCTCAGCCTCCCAAGTAGCTGGGATTACA

AGCATGTGCCACCACACCTGGCTAATTTTCTATTTTTAGTAGAGACGGGT

TTCTCCATGTTGGTCAGCCTCAGCCTCCCAAGTAACTGGGATTACAGGCC

TGTGCCACCACACCCGGCTAATTTTTTCTATTTTTGACAGGGACGGGGTT

TCACCATGTTGGTCAGGCTGGTCTAGA-3'.
```

Figure 1:
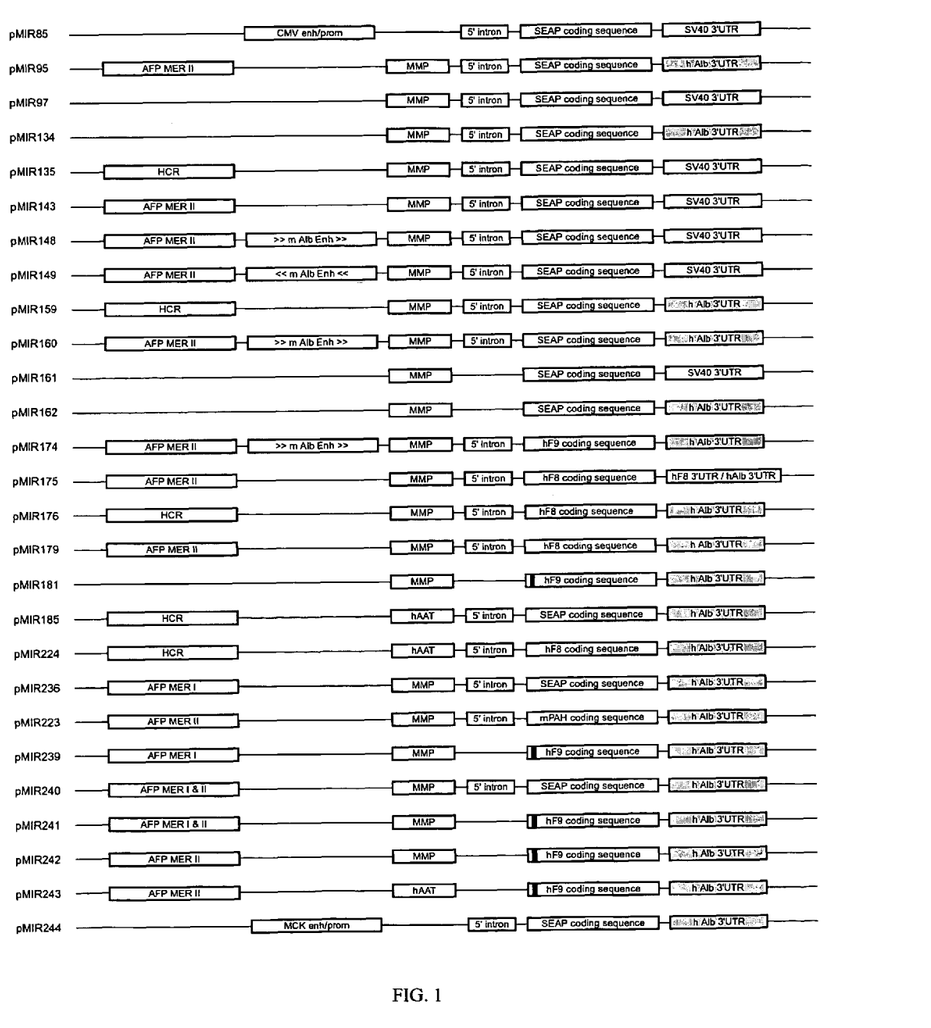

2) Plasmid and gene expression cassettes for evaluation of effect of 3'UTR on transcription. A schematic of these expression cassettes is shown in FIG. 1.

a) Plasmid pMIR85 contains the human SEAP coding sequence from pSEAP2-Basic Vector (Clontech, Palo Alto, Calif.) linked to the CMV enhancer/promoter and 5' chimeric intron from pCI Mammalian Expression Vector (Promega, Madison, Wis.).

b) Plasmid pMIR95 is identical to pMIR143 except that the human albumin 3'UTR containing a truncation in intron 14 replaced the SV40 3'UTR.

c) Plasmid pMIR97 encodes the secreted alkaline phosphatase (SEAP) gene. SEAP expression is driven by the murine minimal promoter from −281 to +39 with a G to A point mutation at position −52. The expression cassette includes a 5' chimeric intron in the 5 untranslated region and the SV40 polyadenylation signal in the 3' untranslated region. The plasmid also contains a prokaryotic promoter driving the kanamycin resistance gene and an origin of replication. Most of the plasmids described are derived from pMIR97. For many of these, enhancer elements were inserted upstream of the minimal promoter using Bgl II and EcoRI sites.

d) Plasmid pMIR134 is identical to pMIR97 except for the 3'UTR. The SV40 3'UTR from pMIR97 was replaced by the human albumin gene 3'UTR (SEQ ID 7) containing a truncation in intron 14.

e) Plasmid pMIR135 contains the ApoE Hepatic Control Region (SEQ ID 9) cloned into the Bgl II and EcoRI sites of pMIR97.

f) Plasmid pMIR143 has the murine AFP minimal enhancer region II (MERII) inserted into the Bgl II and EcoRI sites of pMIR97.

g) Plasmid pMIR148 contains the mouse albumin enhancer cloned into the EcoRI site of pMIR143 in the sense orientation.

h) Plasmid pMIR149 contains the mouse albumin enhancer cloned into the EcoRI site of pMIR143 in the anti-sense orientation.

i) Plasmid pMIR159 is identical to pMIR135 except that the human albumin 3'UTR containing a truncation in intron 14 replaces the SV40 3'UTR.

j) Plasmid pMIR160 is identical to pMIR148 except that the human albumin 3'UTR containing a truncation in intron 14 replaces the SV40 3'UTR.

k) Plasmid pMIR161 is identical to pMIR97 except that the 5' chimeric intron is removed.

l) Plasmid pMIR162 is identical to pMIR134 except that the 5' chimeric intron is removed.

m) Plasmid pMIR174 is identical to pMIR160 except that the human factor IX (hF9) coding sequence replaces the SEAP coding sequence.

n) Plasmid pMIR175 is identical to plasmid pMIR95 except the SEAP coding sequence was replaced by the human factor VIII (hF8) coding sequence and the first 287 by of the factor VIII 3'UTR containing two polyadenylation signals. The hF8 polyadenylation signals are therefore upstream of the albumin 3'UTR. The upstream factor VIII polyadenylation signals would, therefore, preclude inclusion of the truncated albumin intron in the resulting mRNA.

o) Plasmid pMIR176 is identical to pMIR159 except that the human factor VIII (hF8) coding sequence replaces the SEAP coding sequence.

p) Plasmid pMIR179 is identical to pMIR95 except that the human factor VIII (hF8) coding sequence replaced the SEAP coding sequence. In contrast to pMIR175, pMIR179 does not contain any of the hF8 3'UTR, including the polyadenylation signals.
q) Plasmid pMIR181 is identical to pMIR162 except that the human factor IX cDNA with a truncated intron 1 replaces the SEAP cDNA.
r) Plasmid pMIR185 is identical to pMIR159 except that the alpha-1 antitrypsin (hAAT) promoter (−347 to +45) and 5'UTR replaced the albumin promoter and 5'UTR.
s) Plasmid pMIR223 is identical to pMIR179 except that the hF8 coding sequence is replaced by the mouse phenylalanine hydroxylase (mPAH) coding sequence.
t) Plasmid pMIR224 is identical to pMIR176 except that the human alpha-1 antitrypsin promoter from −347 to +45 replaces the albumin promoter.
u) Plasmid pMIR236 is identical to pMIR134 except that the mouse AFP MERI enhancer is inserted into the EcoRI site.
v) Plasmid pMIR239 is identical to pMIR181 except that the mouse AFP MERI is inserted into the EcoRI site upstream of the albumin promoter.
w) Plasmid pMIR240 is identical to pMIR134 except that the PCR product including AFP MERI and MERII in their genomic context are inserted into the EcoR V site.
x) Plasmid pMIR241 is identical to pMIR181 except that the PCR product including AFP MERI and MERII in their genomic context are inserted into the Pme I site.
y) Plasmid pMIR242 is identical to pMIR181 except that the AFP MERIT is inserted into the Bgl II and EcoRI sites.
z) Plasmid pMIR243 is identical to pMIR242 except that the hAAT promoter and 5'UTR replace the albumin promoter and 5'UTR.
aa) Plasmid pMIR244 is identical to pMIR134 except that the albumin promoter has been replaced with the muscle creatine kinase enhancer/promoter from −3352 to +1.

Figure 2:
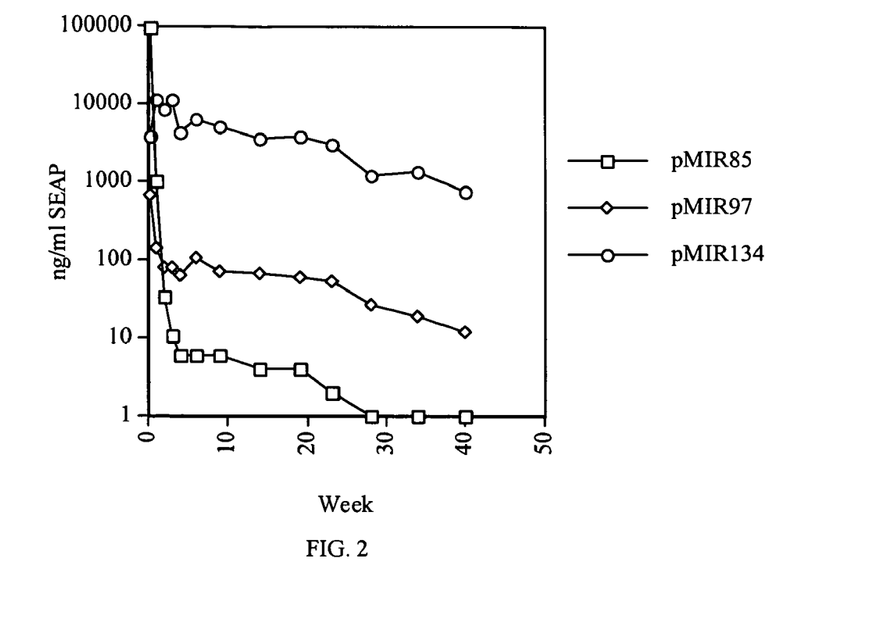
FIG. 2. Expression of SEAP from plasmids with the minimal albumin promoter. Plasmids pMIR97 and pMIR134 have the minimal albumin promoter. pMIR85 has the commonly used CMV enhancer/promoter. Each mouse was injected into the tail vein with 10 plasmid pMIR85, pMIR97 or pMIR134 (n=5). The serum was collected at indicated time points and assayed for SEAP expression. Expression is shown as ng human SEAP/ml mouse serum.
Figure 3:
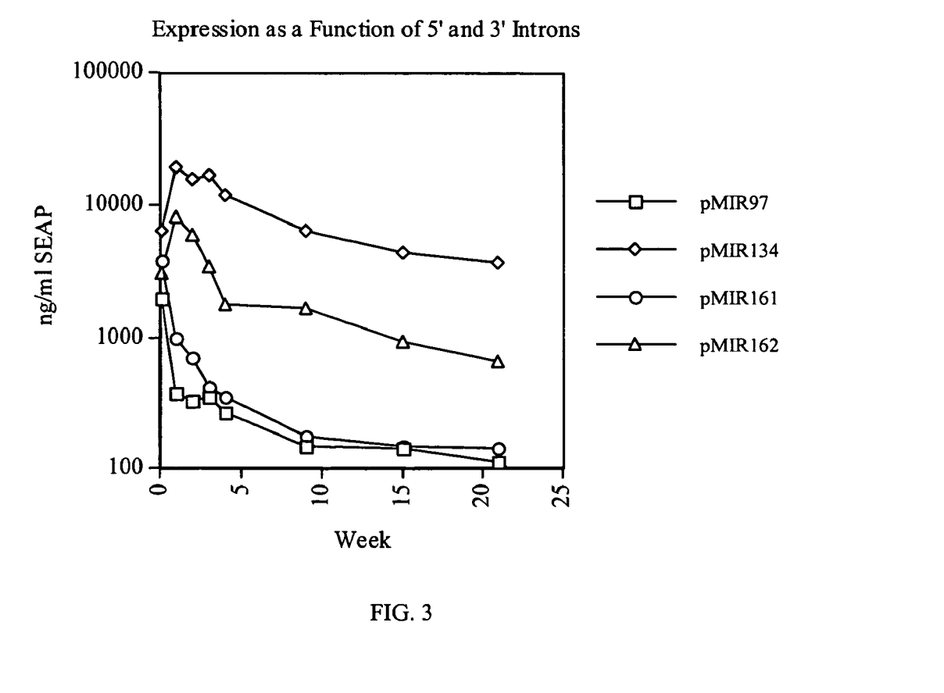
FIG. 3. An intron in the 5 region of the expression cassette increases expression from plasmids that have the albumin 3'UTR. For each sample, five C57B1/6 mice were injected with 10 μg plasmid pMIR97, pMIR134, pMIR161 or pMIR162. The serum was collected at indicated time points and assayed for SEAP expression. Expression is shown as ng human SEAP/ml mouse serum.
Figure 4:
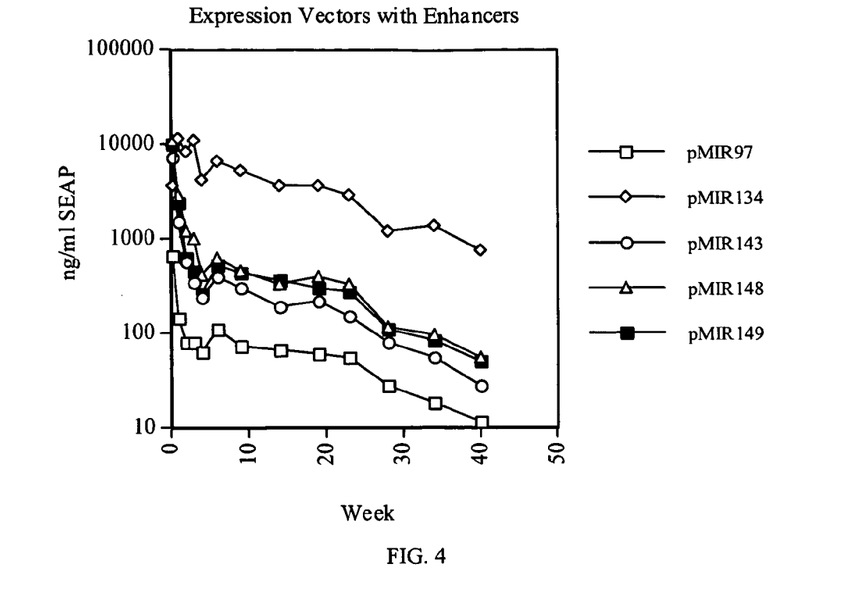

3) Expression of the reporter gene Secreted Alkaline Phosphatase (SEAP). Plasmids encoding SEAP were delivered to C57B1/6 mice by high pressure tail vein injections. Mice were injected into the tail vein with 10 µg plasmid DNA (pDNA) in 2 ml Ringer's Solution (145 mM NaCl, 4 mM KCl, 2 mM $CaCl_2$) in about 7 seconds [Zang et al. Hum Gene Ther. 1999 10(10):1735-1737]. Mice were bled from the retro-orbital sinus at various times after DNA delivery. After clotting, cells and clotted factors were pelleted from the blood to obtain serum. The serum was evaluated for the presence of SEAP by a chemiluminescence assay using the Phospha-Light kit (Tropix, Bedford, Mass.).

a) Comparison of minimal albumin promoter reporter gene expression from plasmids with the albumin or the SV40 3'UTR. SEAP reporter gene plasmids were used to compare expression from vectors that had either the albumin 3'UTR or the SV40 late polyadenylation sequence from pCI Mammalian Expression Vector (Promega, Madison, Wis.). Plasmids pMIR97 and pMIR134 are identical except for the 3'UTR. Both have the minimal mouse albumin promoter with point mutation as in Example 2. Neither has an upstream enhancer. InpMIR97 the 3'UTR is from SV40. pMIR134 has the human albumin gene 3'UTR with a truncated intron 14. pMIR85 has the cytomegalovims (CMV) enhancer/promoter and chimeric intron from pCI Mammalian Expression Vector (Promega, Madison, Wis.). This CMV expression vector was included in the experiment as the standard viral promoter commonly used. It gives initially high expression that declines rapidly in the first few days following injection. Five C57B1/6 mice were injected with each plasmid, 10 µg pDNA per mouse. The average values for SEAP expressed at each time point are shown in FIG. 2. At 21 weeks post injection, the albumin 3'UTR conferred 29-fold higher expression than the SV40 3'UTR on the minimal albumin promoter construct.

b) Effects of a 5' intron. Minimal albumin promoter expression vectors were used to determine the effects on gene expression when an intron was included in the 5' untranslated region. Plasmid pMIR161 differs from pMIR97 only in that the S chimeric intron of pMIR97 was removed. Both plasmids have the SV40 3'UTR. Mice injected with either of these plasmids expressed a similar amount of SEAP nine weeks post injection (FIG. 3). The expression profiles were similar, dropping 12-20 fold between day one and 9 weeks. Plasmids pMIR162 and pMIR134 both have the albumin 3'UTR. The chimeric intron in the 5'UTR of pMIR134 was removed to generate pMIR162. The albumin 3'UTR promotes higher and more stable expression levels than does the SV40 3'UTR for these expression cassettes (FIG. 3). An intron in the 5'UTR increases the level of expression from plasmids that have the albumin 3'UTR(FIG. 3).

c) Enhancers increase expression from the minimal albumin promoter. Enhancers from the albumin gene family were inserted into the minimal albumin promoter expression vector pMIR97 that has the SV40 3'UTR. Plasmids pMIR143, pMIR148 and pMIR149 all include the mouse AFP MERII enhancer element. In addition to AFP MERII, pMIR148 and pMIR149 have the mouse albumin enhancer that is normally located 10 kb upstream of the transcription start site. Both enhancers stimulate expression (FIG. 4). Nine weeks post injection, mice injected with pMIR143 produced 4 times more SEAP than mice injected with the control plasmid pMIR97. Mice injected with either pMIR148 or pMIR149 produced 6 times more SEAP than the pMIR97 control. These results are consistent with the expectation that enhancers function equally well in either orientation. The albumin gene family enhancers, AFP MERII and the mouse (−10 kb) albumin enhancer, function with the albumin promoter to increase expression of the SEAP reporter gene.

Figure 5:
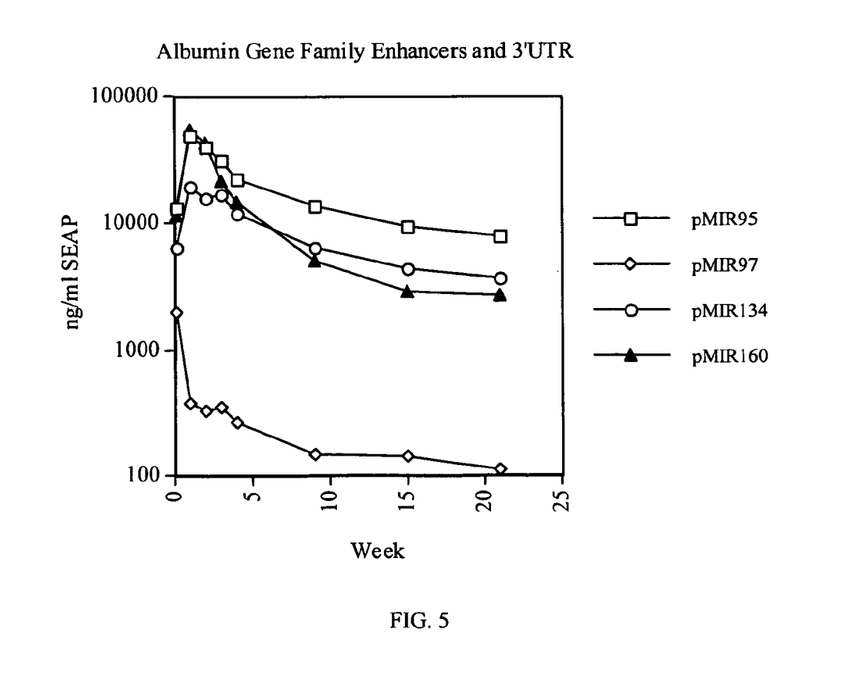
FIG. 5. Enhancers from the albumin gene family stimulate expression from plasmids that include the albumin 3'UTR. C57B1/6 mice were injected with 10 μg plasmid pMIR97, pMIR134, pMIR95, or pMIR160, five mice per sample. The serum was collected at indicated time points and assayed for SEAP expression. Expression is shown as ng human SEAP/ml mouse serum.
Figure 6:
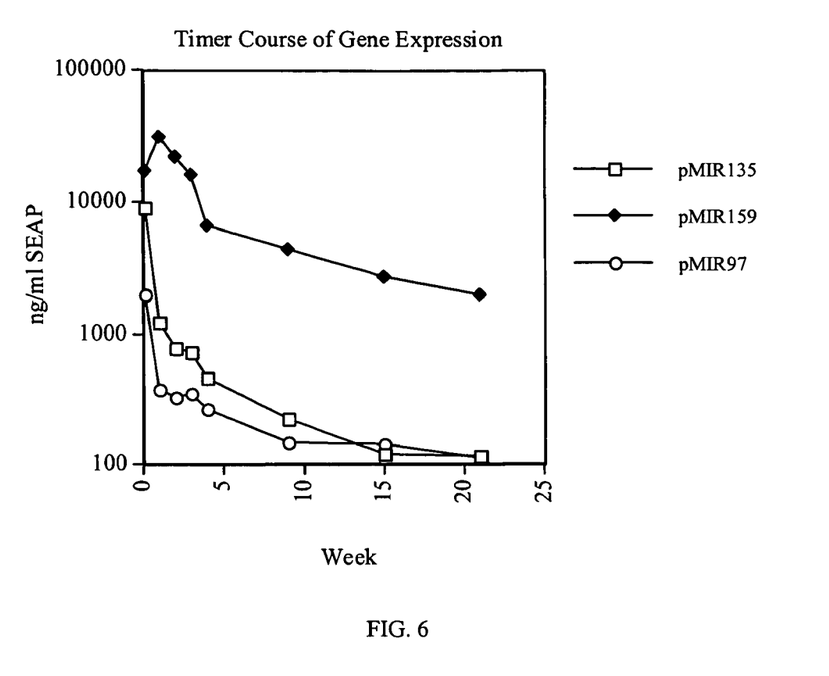

The albumin 3'UTR cassette, pMIR134, without a liver enhancer, gave greater SEAP expression than any of the SV40 3'UTR cassettes with the enhancers.

d) Enhancers increase expression from plasmids that include the albumin 3'UTR. Expression of SEAP reporter gene from plasmids with the SV40 3'UTR, pMIR143, pMIR148, and pMIR149, dropped after the first day post injection. From day one to week 9 the drop was over 20-fold (FIG. 4). In contrast, similar plasmids with the albumin 3'UTR instead of the SV40 3'UTR had increased expression from day one to day 7 (FIG. 5). SEAP expression from pMIR95-containing the AFP MERII enhancer and albumin 3'UTR was slightly higher at 9 weeks than at day one, and by week 21 it was less than two-fold lower than day one. Expression from pMIR160-containing the AFP MERII enhancer, albumin enhancer and albumin 3'UTR-decreased 2-fold from day one to week 9, and only 4-fold from day one to week 21. Expression from pMIR134—with no upstream enhancer—was nearly the same at day one and week 9, with less than a 2-fold decrease in expression from day one to week 21.

e) Expression from the heterologous ApoE hepatic control region (HCR) is stabilized by the albumin 3'UTR. A SEAP reporter gene vector containing the ApoE HCR and minimal albumin promoter showed elevated and more stable gene expression when operable linked to the albumin 3'UTR. Plasmids pMIR135 and pMIR159 are identical except that pMIR135 has the SV40 3'UTR and pMIR159 has the albumin 3' UTR. At day one, expression from pMIR159 was 2-fold higher than that from pMIR135 (FIG. 6). Expression from pMIR159 was 26 times higher than from pMIR135 at day 7, and 19-fold higher at week 9.

f) Function of the albumin 3'UTR with a heterologous promoter in mouse liver. Plasmid pMIR185 is identical to pMIR159 except that the albumin promoter and 5'UTR were replaced with the hAAT promoter and 5'UTR. C57Bl/6 mice would each be injected with 10 μg pMIR185. Serum is collected from the mice at 1, 7, 14, 21, and 28 days and then every four weeks thereafter and assayed for the presence of reporter gene SEAP.

Figure 7:
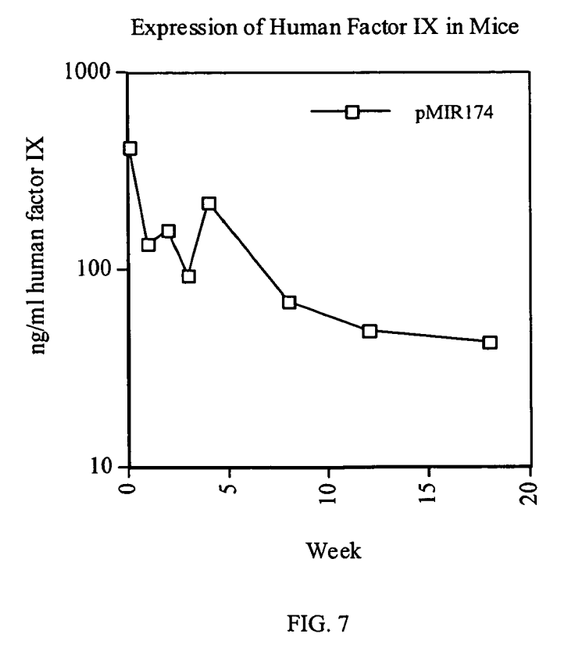
FIG. 7. Expression of Human Factor IX in Mice. C57B1/6 mice were injected into the tail vein with 20 μg pMIR174 encoding human factor IX. At the indicated time, mice were bled and their plasma was evaluated by ELISA to determine the concentration of hF9 that the mice were producing. The average expression of hF9 from 5 mice is shown.

4) Expression of Factor IX. C57B1/6 mice were injected as in example 3 with 20 μg plasmid pMIR174, which has the AFP MERIT enhancer, the mouse albumin (−10 kb) enhancer, the minimal albumin promoter, and the albumin 3'UTR. Mice were bled from the retro-orbital sinus at various times after DNA delivery. The blood was placed in heparinized capillary blood collection tubes (Capiject). Cells were then pelleted from the blood. The resulting plasma was evaluated for the presence of human factor IX using the Cedarlane Laboratories kit with paired antibodies for ELISA—Factor IX. The average amount of expression one day after injection was 420 ng hF9 per ml mouse plasma (n=5). FIG. 7 shows that expression decreased only 10-fold over 18 weeks to an average value of 43 ng/ml, which is about 1% of the normal level. We expect that injection of 100 μg plasmid pMIR174, pMIR242, pMIR239, or pMIR243 would allow for therapeutic levels of factor IX production because expression increases with the amount of DNA delivered and expression from our vectors is stable. 100 plasmid DNA was delivered to mice in the factor VIII studies.

Figure 8:
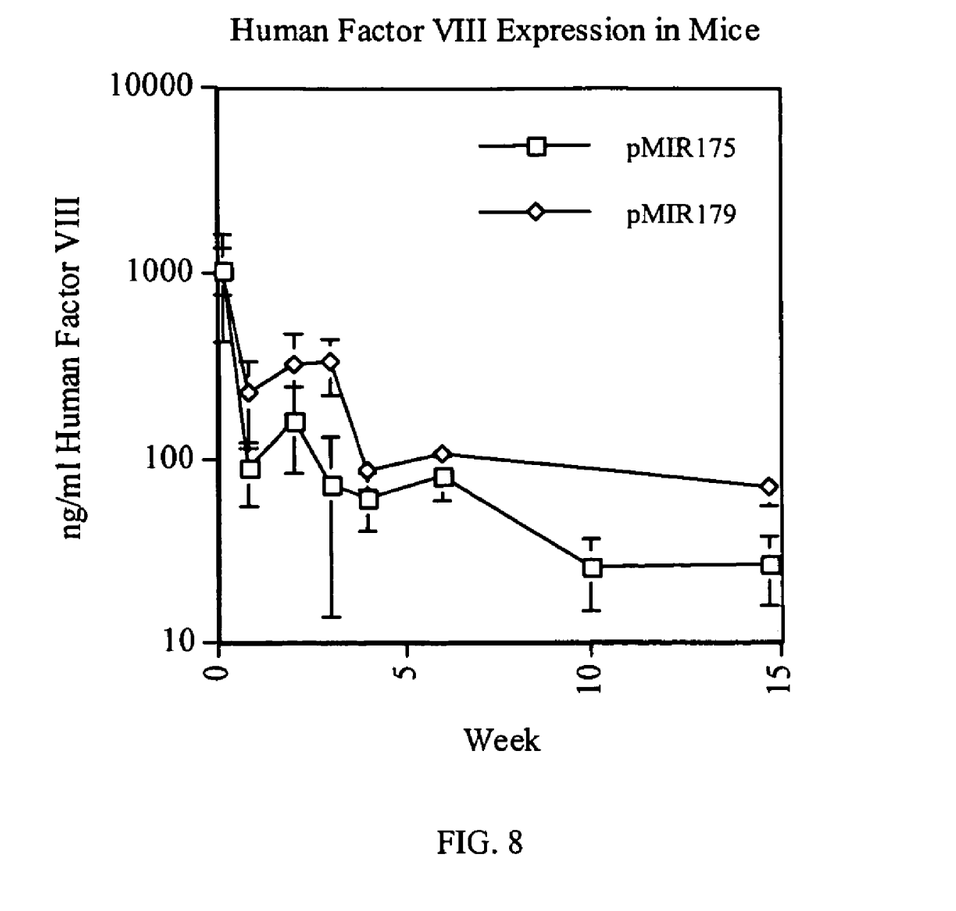
FIG. 8. Expression of human factor VIII in mice. C57B1/6 mice were injected into the tail vein with 100 μg pMIR175 or pMIR179 encoding human factor VIII. At the indicated times, mice were bled and their plasma was evaluated by ELISA to determine the concentration of hF8 that the mice were producing. The average expression of hF8 from 5 mice is shown with error bars.

5) Expression of Factor VIII. C57B1/6 mice were injected with 100 μg pMIR175 or pMIR179 as in example 3. In pMIR 179 the translation stop codon is immediately upstream of the albumin 3'UTR that includes truncated intron 14. In pMIR175 the translation stop codon is followed by 278 by of hF8 3'UTR and then the albumin 3'UTR. The hF8 polyadenylation signals precede the albumin intron and polyadenylation signals. Mice were bled from the retro-orbital sinus at various times after pDNA delivery. The blood was placed in heparinized capillary blood collection tubes (Capiject). Cells were then pelleted from the blood. The resulthg plasma was evaluated for the presence of human factor VIII using the Cedarlane Laboratories kit with paired antibodies for ELISA—Factor VIII. At day one, mice injected with pMIR175 or pMIR179 produced the same amount of hF8, just over 1,000 ng/ml mouse plasma (FIG. 8, n=5). This amount of factor VIII is 5 times higher than the normal endogenous amount. Expression from pMIR179 was more stable than expression from pMIR175. After 14 weeks, the average expression from pMIR175 had dropped 39-fold, while expression from pMIR179 dropped only 14-fold. Furthermore, the variation in expression between mice was much lower in mice injected with pMIR179. After 14 weeks, the pMIR179 injected mice expressed 71±16 ng/ml hF8. Mice injected with pMIR175 produced 27±11 ng/ml hF8. Thus, the intron-containing albumin 3'UTR enhances expression of an hF8 transgene in the liver.

100 μg Factor VII-producing plasmid pMIR224—with the hAAT promoter and 5'UTR replacing the albumin promoter and 5'-UTR would be injected into the tail vein of C57B1/6 mice. Blood would be collected at 1, 7, 14, 21, and 28 days post injection and then every 4 weeks thereafter. The plasma is evaluated for hF8 by ELISA.

6) Expression of mouse phenylalanine hydroxylase (mPAH). Hyperphenylalaninemic Pah$^{enu2}$ homozygous mice are a well-characterized model for human phenylketonuria. These knockout mice would be used to evaluate the expression of plasmid pMIR223. Each mouse is injected with 100 μg pMIR223. At various times the blood is collected and assayed for mPAH by ELISA.

7) Long term expression in muscle. Plasmids pMIR85, pMIR95, pMIR97, pMIR134, and pMIR244 would be individually delivered intravascularly to skeletal muscle cells in rats [Budker et al. Gene Ther. 1998 5(2):272-276]. Plasmid pMIR244 contains a muscle specific promoter in combination with the albumin 3'UTR. Each rat is injected with 500 μg DNA into the iliac artery of the hind limb. Blood is collected at various time points and the serum evaluated for the presence of human SEAP expressed from the reporter gene.

A similar plasmid, in which the dystrophin coding sequence replaces the SEAP coding sequence, is delivered to skeletal muscle in mdx muscular dystrophy model mice and long term expression of the dystrophin gene in assayed. Each of these plasmid may be altered to replace the albumin 3'UTR with a intron-containing muscle specific 3'UTR.

REFERENCES

Budker V, Zhang G, Danko I, Williams P, Wolff J. The efficient expression of intravascularly delivered DNA in rat muscle. Gene Ther. 1998 5(2):272-276.

Camper S A, Tilghman S M. Postnatal repression of the alpha-fetoprotein gene is enhancer independent. Genes Dev. 1989 3(4):537-546.

Crowe A J, Sang L, Li K K, Lee K C, Spear B T, Barton M C. Hepatocyte nuclear factor 3 relieves chromatin-mediated repression of the alpha-fetoprotein gene. J Biol Chem. 1999 274(35):25113-25120.

Godbout R, Ingram R S, Tilghman S M. Fine-structure mapping of the three mouse alpha-fetoprotein gene enhancers. Mol Cell Biol. 1988 8(3):1169-1178.

Herweijer H, Zhang G, Subbotin V M, Budker V, Williams P, Wolff J A. Time course of gene expression after plasmid DNA gene transfer to the liver. J Gene Med. 2001 3(3): 280-291.

Kay M A, High K. Gene therapy for the hemophilias. Proc Natl Acad Sci USA. 1999 96(18):9973-9975.

Nishio H, Heiskanen M, Palotie A, Belanger L, Dugaiczyk A. Tandem arrangement of the human seam albumin multigene family in the sub-centromeric region of 4q: evolution and chromosomal direction of transcription. J Mol Biol. 1996 259(1):113-119.

Pinkert C A, Omitz D M, Brinster R L, Palmiter R D. An albumin enhancer located 10 kb upstream functions along with its promoter to direct efficient, liver-specific expression in transgenic mice. Genes Dev. 1987 1(3):268-276.

VandenDriessche T, Collen D, Chuah M K. Viral vector-mediated gene therapy for hemophilia. Curr Gene Ther 2001 September; 1(3):301-315.

Vorachek W R, Steppan C M, Limai M, Black H, Bhattacharya R, Wen P, Kajiyama Y Locker J. Distant Enhancers Stimulate the Albumin Promoter through Complex Proximal Binding Sites. J Biol Chem 2000 275(37):29031-29041

Xu Z L, Mizuguchi H, Ishii-Watabe A, Uchida E, Mayumi T, Hayakawa T. Optimization of transcriptional regulatory elements for constructing plasmid vectors. Gene. 2001 272 (1-2):149-56.

Yew N S, Przybylska M, Ziegler R J, Liu D, Cheng S H. High and sustained transgene expression in vivo from plasmid vectors containing a hybrid ubiquitin promoter. Mol Ther. 2001 4(475-82.

Zhang G, Budker V, Wolff J A. High levels of foreign gene expression in hepatocytes after tail vein injections of naked plasmid DNA. Hum Gene Ther. 1999 10(10):1735-1737.

We claim:

1. An expression cassette for long term in vivo expression of a transgene in a mammalian liver cell wherein the expression cassette comprises the coding sequence of said transgene and SEQ ID NO:7 operatively linked to the 3' end of said coding sequence.

2. An in vitro mammalian liver cell transfected with a gene expression cassette wherein said expression cassette comprises a coding sequence of a transgene and SEQ ID NO:7 operatively linked to the 3' end of said coding sequence.

3. A process for increasing long term in vivo expression of a transgene in a mammalian liver cell comprising: a) constructing a gene expression cassette wherein SEQ ID NO:7 is operatively linked to the 3' end of the coding sequence of said transgene: and, b) delivering said gene expression cassette to the liver cell in vivo wherein long term expression of said transgene is increased.

4. The process of claim 3 wherein the liver cell is a hepatocyte.

5. A gene expression cassette comprising: an alpha-fetoprotein (AFP) enhancer, an albumin promoter, a 5' intron, a linker sequence into which a gene coding sequence can be cloned, and SEQ ID NO:7 operatively linked to the 3' end of said linker sequence.

* * * * *